(12) United States Patent
Peterson

(10) Patent No.: US 6,177,000 B1
(45) Date of Patent: Jan. 23, 2001

(54) BIOSENSOR COMPRISING A LIPID MEMBRANE CONTAINING GATED ION CHANNELS

(75) Inventor: Ian Robert Peterson, Kenilworth (GB)

(73) Assignee: Coventry University, Coventry (GB)

( * ) Notice: Under 35 U.S.C. 154(b), the term of this patent shall be extended for 0 days.

(21) Appl. No.: 09/445,817

(22) PCT Filed: Jun. 15, 1998

(86) PCT No.: PCT/GB98/01738

§ 371 Date: Mar. 13, 2000

§ 102(e) Date: Mar. 13, 2000

(87) PCT Pub. No.: WO98/58248

PCT Pub. Date: Dec. 23, 1998

(30) Foreign Application Priority Data

Jun. 14, 1997 (GB) .................................................. 9712386

(51) Int. Cl.[7] .................................................. G01N 27/26
(52) U.S. Cl. ...................... 205/777.5; 204/403; 204/412; 427/2.13
(58) Field of Search .................................... 204/403, 415, 204/418, 412; 205/778, 793, 775; 427/2.11, 2.13

(56) References Cited

U.S. PATENT DOCUMENTS

| 5,111,221 | 5/1992 | Fare et al. ............................... 357/25 |
| 5,401,378 | 3/1995 | King et al. ............................ 204/418 |
| 5,436,170 | 7/1995 | Cornell et al. ....................... 436/527 |
| 5,693,477 | 12/1997 | Cornell et al. ......................... 435/7.1 |
| 5,736,342 | 4/1998 | Van Wie et al. ...................... 435/7.2 |
| 5,741,712 | 4/1998 | Cornell et al. ....................... 436/501 |
| 5,756,355 | 5/1998 | Lang et al. .......................... 435/7.21 |
| 5,766,960 | 6/1998 | Cornell et al. ....................... 436/501 |

*Primary Examiner*—T. Tung
*Assistant Examiner*—Alex Noguerola
(74) *Attorney, Agent, or Firm*—Oppenheimer Wolff & Donnelly LLP

(57) ABSTRACT

A biosensor has a lipid membrane (7) containing gated ion channels sensitive to the presence or otherwise of an analyte molecule in a sample applied, in use, to a first side of the lipid membrane (7). The lipid membrane (7) is disposed between a pair of electrodes (1, 2) in which a first layer of porous gel (4) is applied to the first side of the lipid membrane (7).

16 Claims, 1 Drawing Sheet

BIOSENSOR COMPRISING A LIPID MEMBRANE CONTAINING GATED ION CHANNELS

This invention relates to a biosensor, and in particular to a biosensor of the type which operates by detecting or measuring the transport of ions across a lipid membrane.

Biosensors based on the use of a gated channel protein spanning a bilayer membrane are of considerable interest. Each individual binding event can give rise to the passage of as many as $10^9$ individual ions through the channel during a practical measurement interval. Also, the operation of distinct channels is essentially independent and the currents through them combine linearly. These two factors inspire the hope of a general principle for sensing biomolecules which displays both excellent sensitivity and high dynamic range.

In order to achieve high dynamic range it is necessary to choose channel proteins which open in the presence of the target biomolecule. This is the case for a number of naturally-occurring channel proteins, typically neurotransmitter receptors in nerve cells. In a more generally applicable approach, robust ungated channels, particularly the gramicidins, are bound chemically to antibody molecules in such a way as normally to obstruct the channel, and to unblock it when an antigen binds.

The electric charge transported through these channel proteins consists physically of solvated ions. In order to allow further processing, the ions must be exchanged for the flow of electrons through a wire at electrodes located at both the front and rear of the bilayer. In one known approach, the bilayer is located immediately adjacent to the rear noble-metal electrode. It is not clear where the ions flow to. If they discharge at the electrode, the associated chemical changes will inevitably lead to degradation.

In another known approach, there is electrolyte behind the bilayer contained in a gel. The bilayer is fabricated by a standard technique across an aperture adjacent to the gel. The gel provides some physical support for the bilayer, so that it is able to withstand quite vigorous agitation of the test liquid. However the bilayer cannot be dehydrated and must be formed immediately prior to the measurement in the aqueous medium to be monitored. It is directly exposed to the medium and cannot withstand contact with a solid.

There has now been devised a novel form of biosensor based on measurement of ion transport across a lipid membrane which overcomes or substantially mitigates the disadvantages of known forms of such biosensor.

According to a first aspect of the invention, a biosensor comprises a lipid membrane containing gated ion channels sensitive to the presence or otherwise of an analyte molecule in a sample applied, in use, to a first side of said lipid membrane, the lipid membrane being disposed between a pair of electrodes, wherein a first layer of a porous gel is applied to the first side of the lipid membrane.

The biosensor according to the invention is advantageous primarily in that the first layer of porous gel applied to the lipid membrane protects the membrane from dehydration and physical damage caused by mechanical contact, yet still permits molecules contained within the sample access to the lipid membrane. Because the membrane is not destroyed by drying of the biosensor, the biosensor can be packaged and stored in the dry state, for rehydration immediately prior to use.

Preferably, a second layer of gel is also applied to the second side of the lipid membrane, to further protect the membrane and to provide the necessary separation from the adjacent electrode and to accommodate a reservoir of ions required by that electrode.

The gel is preferably a biocompatible and porous gel, most preferably a hydrogel. Suitable gel materials include agarose, dextran, carrageenan, alginic acid, starch, cellulose, or derivatives of these such as eg carboxymethyl derivatives, or a water-swellable organic polymer such as eg polyvinyl alcohol, polyacrylic acid, polyacrylamide or polyethylene glycol. A particularly preferred gel material is agarose. Other gel materials considered particularly suitable include polyacrylaimide gels.

The thickness of particularly the first layer of gel is preferably such as to permit diffusion of biomolecules of approximately 1 kD to occur in reasonably short time periods, eg less than 5 minutes, more preferably less than 2 minutes. The first and second layers of gel preferably have thicknesses of less than 5 mm, eg 0.1 to 2 mm, most preferably approximately about 1 mm.

The lipid membrane is preferably a bilayer of amphiphilic molecules, most preferably one or more phospholipids, eg phosphatidylcholines and/or phosphatidylethanolamines. The lipids may have hydrocarbon tails with chain lengths of $C_{12}$–$C_{22}$, most preferably $C_{12}$–$C_{18}$. A particularly preferred phospholipid is dioleylphosphatidylcholine. Other membrane forming molecules which may be employed include amphiphilic polymers, eg hydrophobic polymer chains with hydrophilic side groups. One example of such a polymer is a polysiloxane with phosphatidylcholine side groups.

Suitable molecules defining the gated ion channels are incorporated into the lipid membrane, eg membrane-bound proteins.

Preferably a perforated sheet of an inert and impermeable material is interposed between the lipid membrane and the second gel layer. A suitable such material is polytetrafluoroethylene. The sheet is preferably thin, eg less than about 100 $\mu$m in thickness, more preferably about 10 $\mu$m in thickness. The sheet is preferably formed with one or more perforations of diameter 10–200 $\mu$m, more preferably about 50–100 $\mu$m. The sheet of material permits the flow of current between the electrodes only in the region of the perforation(s) in the sheet.

The lipid membrane may be formed by dissolving the membrane-forming lipid and the molecules defining the gated ion channels in a solvent and applying the solution so formed to the second gel layer (or to the perforated sheet of inert material abutting the second gel layer). Any suitable solvent may be used, provided that it is substantially immiscible with water. Polar solvents, capable of initiating hydrogen bonds, are preferred since their use provides a strong driving force for complete coverage of the solution over the surface. A particularly preferred solvent is chloroform. The solution preferably has a concentration of 0.01 to 5% w/v, more preferably less than 1% w/v, eg about 0.2% w/v.

However, the method of forming the lipid membrane described above may not always be suitable. For example, some ligand-gated channel proteins may be denatured by chloroform. One alternative method for the formation of the lipid membrane which may be suitable in such cases involves forming an inverted micellar solution or emulsion containing the membrane forming lipid and molecules defining the gated ion channels, the micellar solution or emulsion having a hydrocarbon continuous phase. The hydrocarbon is preferably an alkane, most preferably hexane.

One functional ligand-gated channel protein for which the alternative method described in the immediately preceding paragraph may be applicable is the nicotinic acetycholine receptor (nAChR—see G Puu et al, *Biosens. Bioelectron.* 10 (1995), 463). This neuroreceptor, with many slight variations, is found in most animals with nervous systems, and a very rich source of supply is available in the electric organ of the common marbled ray *Torpedo marmorata*. A crude extract formed by homogenizing the electric organ of the ray and centrifuging in a CsCl gradient to isolate the membrane-bound fraction has a continuous phase which is essentially aqueous. By reducing the proportion of water it is possible to invert the emusion and to prepare from it an inverse emulsion with a hydrocarbon continuous phase having the characteristics required for formation of the lipid membrane.

The electrodes are preferably noble metal electrodes of generally conventional form. Most preferably the electrodes are silver/silver chloride electrodes formed on sheets of a suitable substrate such as mica. Preferably the electrode on the first side of the lipid membrane is formed with an aperture which serves as a sample introduction port. Where the device comprises a perforated sheet of material as described above, the aperture is preferably aligned with the perforation(s).

The invention further provides a method of qualitatively or quantitatively determining an analyte molecule in a sample, which method comprises applying the sample to the first layer of porous gel in a biosensor according to the first aspect of the invention.

The biosensor of the invention is most preferably assembled by coating each of two planar electrodes with a layer of porous gel, placing a solution or emulsion containing lipid molecules onto the second gel layer, and then placing one electrode on the top of the other such that the gel layers are diposed between them. Generally, the biosensor is assembled under the conditions such that the lipid membrane forms spontaneously. Monolayers of lipid will form at the interfaces between the solution or emulsion and the respective gel layers. As the bulk solution or emulsion is expelled or evaporates from between the gel layers the two monolayers come together to form the lipid membrane bilayer.

A preferred embodiment of the invention will now be described in greater detail, by way of example only, with reference to the accompanying Figures, in which FIG. 1 is a schematic sectional side view of a biosensor cell according to the invention;

FIG. 2 shows a bar histogram of cell resistances (logarithmic resistance scale) measured using a cell of the type shown in FIG. 1, with and without a lipid bilayer; and FIG. 3 shows a scatter plot of measured cell resistance (log scale) measured using the cell of FIG. 1 after long exposure to gramicidin, versus the time taken for the resistance to reach its ultimate value.

Referring first to FIG. 1, a biosensor cell according to the invention is formed between a pair of planar Ag/AgCl electrodes 1,2 formed on mica substrates 1*a*,2*a* as described below. The upper mica substrate 1*a* has a 3 mm diameter aperture 3 through which test samples may be introduced. The space between the electrodes 1,2 is filled by first and second layers 4,5 of agarose gel (prepared as described below) separated by a 10 μm thick PTFE sheet 6 on the upper surface of which is formed a lipid bilayer 7. The sheet 6 has at least one perforation 10. Silver wires 8,9 are connected to the electrodes 1,2.

Formation of Gel Sheets

A mixture of 1% by weight agarose, 10% by weight glycerol, 0.1M NaCl, 0.1M KCl and 0.01M CaCl$_2$ and the remainder ultrapure water were heated to boiling point. While still liquid the mixture was pipetted into a hydrophilic glass mould or surface (typically 6 ml) and allowed to set.

The gel sheets 4,5 were 1 mm thick on initial formation. They were allowed to dehydrate completely under laminar flow of ambient air (nominal 23° C. 50% relative humidity). After rehydration with electrolyte (0.1M NaCl, 0.1M KCl, 0.01M CaCl$_2$ in ultrapure water) the gel was removed from its substrate.

Formation of Electrodes

The silver/silver chloride electrodes 1,2 were fabricated as follows. Freshly-cleaved pieces of mica 1*a*,2*a* were perforated as required (typically 3 mm diameter holes in a piece of a few centimetres in size). They were rinsed and sonicated separately with chloroform and methanol. A 12.5 μm-diameter silver wire 8,9 was placed on the surface which was then coated with silver dag and allowed to dry, securing the wire 8,9. The surface was electrolytically chlorided in 1M HCl at 9V using a stainless steel counterelectrode, initially as the cathode for 10 s and then as the anode for a further 10 s. The rehydrated gel layer 4,5 described in the previous paragraph was placed in contact with the silver side.

Assembly of Biosensor Cell

10 μm-thick PTFE film 6 was cut into cm-size pieces and perforated with a red-hot tungsten tip. The resulting holes were typically 50–100 μm in diameter.

A spreading solution was made up from L,α-dioleylphosphatidylcholine at a concentration of 20 g/l in chloroform.

A structure shown in FIG. 1 was assembled as follows. The perforated piece of PTFE 6 was placed on the lower electrode 2 with its gel coating 5. 10 μl of spreading solution was spread over the PTFE 6 and a second, apertured electrode 1 with its gel coating 4 placed on top, ensuring that the aperture 3 was aligned with a perforation in the PTFE sheet 6.

Measurements

For measurement, the electrolytic bilayer cells produced by the above procedure were placed in a electrically-shielded box and a drop of test solution placed over the mica aperture. The resistance of the cells was measured with a Keithley Model 175 digital multimeter. To measure the variation of current as a function of time, the cell current was converted to a voltage using a Bio-Logic BLM-120 bilayer membrane amplifier with a transimpedance of 1.0 GΩ. The output voltage was digitised by a Cambridge Electronic Design 1401 Plus multichannel analyser and logged by a computer running the CDR program.

Figure 1:
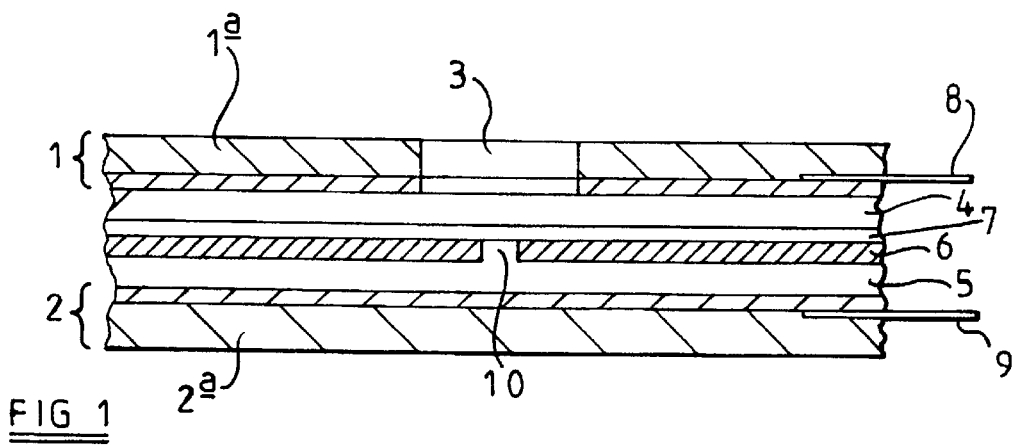
Figure 2:
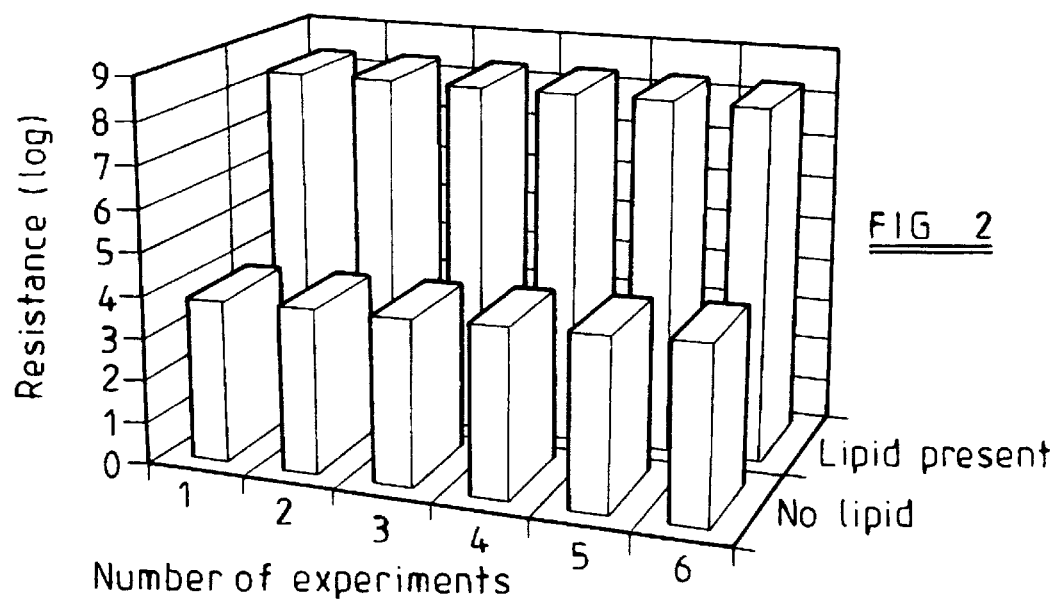
FIG. 2 shows the results of six measurements of the resistance of the cell prepared as described above, contrasted with measurements made in the absence of a lipid membrane. As can be seen, the effect of the lipid membrane is to increase the measured resistance considerably.
Figure 3:
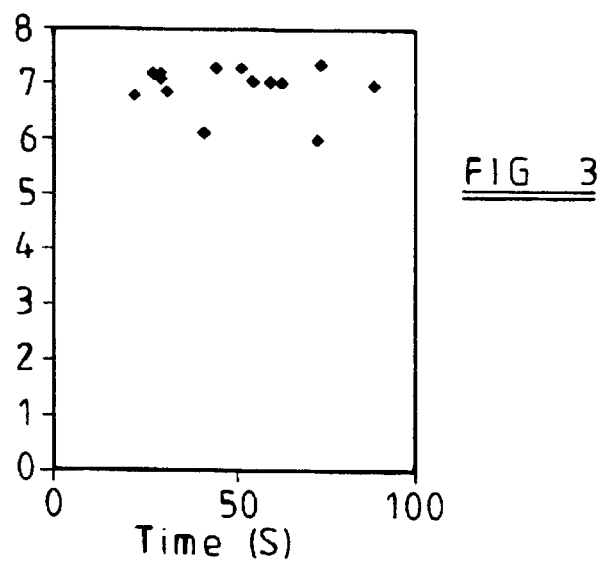
FIG. 3 shows measured resistance values for a cell prepared as described above, after long exposure to a 1 g/l solution of gramicidin-D. The effect of the protein is to reduce the cell resistance.

What is claimed is:

1. A biosensor comprising a lipid membrane containing gated ion channels sensitive to the presence or otherwise of an analyte molecule in a sample applied, in use, to a first side of said lipid membrane, the lipid membrane being disposed between a pair of electrodes, wherein the first side of the lipid membrane is coated with a first layer of porous get and the second side of the lipid membrane is coated with a second layer of porous gel.

2. A biosensor as claimed in claim 1, wherein the gel is a hydrogel.

3. A biosensor as claimed in claim 2 wherein the first layer of gel is such as to permit diffusion of biomolecules of approximately 1 kD to occur in less than 5 minutes.

4. A method of qualitatively or quantitatively determining an analyte molecule in a sample, which method comprises applying the sample to the first layer of porous gel in a biosensor according to claim 3.

5. A biosensor as claimed in claim 2 wherein the lipids of the lipid membrane have hydrocarbon tails with chain lengths of $C_{12-22}$.

6. A method of qualitatively or quantitatively determining an analyte molecule in a sarnple, which method comprises applying the sample to the first layer of porous gel in a biosensor according to claim 2.

7. A biosensor as claimed in claim 1 wherein the first layer of gel is such as to permit diffusion of biomolecules of approximately 1 kD to occur in less than 5 minutes.

8. A biosensor as claimed in claim 7 wherein the lipids of the lipid membrane have hydrocarbon tails with chain lengths of $C_{12-22}$.

9. A method of qualitatively or quantitatively determining an analyte molecule in a sample, which method comprises applying the sample to the first layer of porous gel in a biosensor according to claim 7.

10. A biosensor as claimed in claim 1 wherein the lipids of the lipid membrane have hydrocarbon tails with chain lengths of $C_{12-22}$.

11. A method of qualitatively or quantitatively determining an analyte molecule in a sample, which method comprises applying the sample to the first layer of porous gel in a biosensor according to claim 1.

12. A method of assembling a biosensor comprising coating each of two planar electrodes with a layer of porous gel, placing lipid solution on to one of said layers and then placing one electrode on top of the other such that the gel layers are disposed between them and are separated by a lipid membrane.

13. A method as claimed in claim 12 wherein prior to the formation of the lipid membrane the membrane-forming lipid and the molecules defining gated ion channels are dissolved in a solvent.

14. A method as claimed in claim 13 wherein the solvent is chloroform.

15. A method as claimed in claim 12 wherein, prior to the formation of the lipid membrane the membrane-forming lipid and molecules defining gated ion channels are incorporated into an inverted emulsion with an alkane-rich continuous phase.

16. A method as claimed in claim 15 wherein the alkane is hexane.

* * * * *